US008603395B2

(12) United States Patent
Fries et al.

(10) Patent No.: US 8,603,395 B2
(45) Date of Patent: *Dec. 10, 2013

(54) SELF-PROPELLED SENSOR APPARATUS FOR IN SITU ANALYSIS OF ENVIROMENTAL PARAMETERS

(75) Inventors: David P Fries, St. Petersburg, FL (US); Michelle L Janowiak, Clearwater, FL (US); George Steimle, St. Petersburg, FL (US); Heather A Broadbent, St. Petersburg, FL (US)

(73) Assignee: University of South Florida, Tampa, FL (US)

(*) Notice: Subject to any disclaimer, the term of this patent is extended or adjusted under 35 U.S.C. 154(b) by 1065 days.

This patent is subject to a terminal disclaimer.

(21) Appl. No.: 12/615,800

(22) Filed: Nov. 10, 2009

(65) Prior Publication Data

US 2010/0058842 A1    Mar. 11, 2010

Related U.S. Application Data

(60) Division of application No. 10/908,749, filed on May 25, 2005, now abandoned, which is a continuation of application No. PCT/US03/37480, filed on Nov. 25, 2003, now abandoned, which is a continuation of application No. 10/303,522, filed on Nov. 25, 2002, now abandoned, and a continuation of application No. 10/319,683, filed on Dec. 13, 2002, now abandoned.

(51) Int. Cl.
G01N 15/06 (2006.01)
G01N 1/10 (2006.01)
G01N 1/00 (2006.01)

(52) U.S. Cl.
USPC ....... 422/68.1; 422/534; 422/535; 73/863.21; 73/868.23; 73/863.73; 73/61.59; 73/61.61; 436/43; 436/174; 436/180; 210/220; 210/661; 210/662

(58) Field of Classification Search
USPC ................. 422/68.1, 63, 509, 513, 534, 535; 436/174, 180, 43; 210/220, 661–662, 210/767, 97; 73/863.21, 863.23, 863.02, 73/61.58, 61.59, 61.61
See application file for complete search history.

(56) References Cited

U.S. PATENT DOCUMENTS

| | | |
|---|---|---|
| 3,537,316 A | 11/1970 | Stewart et al. |
| 4,144,032 A | 3/1979 | Davis, Jr. |
| 4,226,115 A | 10/1980 | Williams et al. |
| 4,713,967 A | 12/1987 | Overs et al. |
| 5,167,802 A | 12/1992 | Sandstrom et al. |
| 5,223,439 A | 6/1993 | Rolle |
| 5,481,927 A | 1/1996 | Hubbell et al. |

(Continued)

OTHER PUBLICATIONS

Singer, N. Flying SnifferSTAR may aid civilians and US military. Sandia National Laboratories. Jan. 23, 2003.

(Continued)

*Primary Examiner* — Brian R Gordon
(74) *Attorney, Agent, or Firm* — Nicholas Pfeifer; Smith & Hopen, P.A.

(57) ABSTRACT

A self-propelled apparatus for analyzing a component contained in a fluid medium. The self-propelled apparatus uses kinetic energy of the apparatus to drive a fluid under analysis through the apparatus. This is accomplished by use of a conveyance system that is attached to the analytical system of the apparatus. A sensor system is used to analyze the component collected within the confines of an analysis chamber, a part of the analysis system. The invention also includes a method of using the analytical apparatus.

22 Claims, 3 Drawing Sheets

(56) References Cited

U.S. PATENT DOCUMENTS

| | | |
|---|---|---|
| 5,804,743 A | 9/1998 | Vroblesky et al. |
| 5,844,147 A | 12/1998 | Fiedler et al. |
| 6,177,672 B1 | 1/2001 | Lin et al. |
| 6,272,938 B1 | 8/2001 | Baghel et al. |
| 6,276,220 B1 | 8/2001 | Varhol |
| 6,306,350 B1 | 10/2001 | Mereish et al. |
| 6,321,609 B1 | 11/2001 | Mengel et al. |
| 6,354,135 B1 | 3/2002 | McGee et al. |
| 6,458,267 B2 | 10/2002 | Kaendler |

OTHER PUBLICATIONS

Hoover, A. Student-Built Projectile Could Help Soldiers Detect Bombs, Chemicals. UF News. Apr. 28, 2004.

SELF-PROPELLED SENSOR APPARATUS FOR IN SITU ANALYSIS OF ENVIROMENTAL PARAMETERS

CROSS REFERENCE TO RELATED APPLICATIONS

This application is a divisional of currently pending U.S. patent application Ser. No. 10/908,749 filed May 25, 2005, which is a continuation of International Application No. PCT/US03/37480, filed Nov. 25, 2003 which claims the benefit of U.S. patent application Ser. No. 10/303,522, filed Nov. 25, 2002, and U.S. patent application Ser. No. 10/319,683, filed Dec. 13, 2002, which are all herein incorporated by reference.

STATEMENT OF GOVERNMENT INTEREST

This invention was made with Government support under Grant No. ONR-N0014-98-1-0848 awarded by the Department of the Navy. The Government has certain rights in the invention.

FIELD OF INVENTION

This invention relates to the analysis of biological or chemical, particle or physical species contained in fluid milieus that include trace amount of the species; more specifically, the invention relates to an analytical system having a conveyance system to convey the analytical system through a liquid medium to collect and/or detect desired components and a related method of analyzing the collected components.

BACKGROUND

In recent years the presence of contaminants in bodies of water, both fresh and salt varieties, has become an issue of both public and governmental interest. In addition, air quality with respect to pollution from industrial or bellicose activities deeply affects the daily lives of most of the world's population. With the changing political situation in the world as well as concern over contamination from industrial and agricultural activity, a new intense interest has developed in monitoring water and air sources for pollutants and trace quantities of materials. As technology progresses, it has become increasingly important to know immediately the content of a body of water or air, thus necessitating the development of new analytical systems to give precise information on the presence and/or quantities of microbial and chemical contaminants.

To date, the available methods and devices have been concerned with "capturing" a sample for transportation to a laboratory for analysis and, in the case of trace quantities, concentration of the suspect species for that analysis. In addition, many of the available devices include sophisticated sensors and pumping apparatus that make the devices cumbersome as well as expensive to assemble and to maintain. Even though towed or tethered samplers are known in the art, their uses have been limited to physical characteristics and not the monitoring of chemical or biological species.

U.S. Pat. No. 3,537,316 to Stewart et al. shows a towed underwater sampler having an internal cavity that houses sensor circuits. In this device, water is permitted to flow through the analysis chamber so that temperature and pressure may be evaluated. However, the sensors here are measuring physical parameters and not the chemical or biological content of the water passing through the sensor cavity. In fact, there is no actual sample reading made by the instrument because only the desired parameters of temperature and pressure are immediately evaluated, and the actual sample is captured in a bottle for later analysis.

Another towed sensor system is disclosed in U.S. Pat. No. 4,713,967 to Overs et al. Again the sensors are only concerned with physical properties—temperature and water speed. The temperature and speed are then equated to the presence of fish bait, but no information is obtained about any compositional make-up of the environment or the nature of the fish bait itself.

Inner chambers in contaminant sensing devices for water analysis are described previously as well. One example is U.S. Pat. No. 6,272,938 to Baghel et al. Baghel et al. describes an inner chamber formed by a semi-permeable membrane in communication with an inner chamber containing a sensor that monitors contaminants in a tethered-style apparatus. Water diffuses through the membrane until a threshold is reached and then the diffusion is stopped. In this system, the quantity of contaminants is a function of diffusion time and, thus, is controlled by an unpredictable parameter.

U.S. Pat. No. 6,306,350 to Mereish et al. describes a portable water sampling device that captures the sample in a chamber that is then removed and sent to a lab for analysis. The concentration of the sample is determined as a function of time, because a timer is used to determine the sample collection period. A pump is also used to force the water being tested into the system and past the extraction membrane.

Similar devices that incorporate sampling chambers are described in U.S. Pat. Nos. 5,844,147 to Fiedler et al. and 5,167,802 to Sandstrom et al. Again, the samples are collected and sent to a remote lab for analysis.

In addition to aquatic environments, similar devices have been used in the atmosphere. Examples of these are U.S. Pat. No. 6,321,609 to Mengel et al. and U.S. Pat. No. 6,354,135 to McGee et al. Again, these systems include suction devices or pumps to facilitate the flow of effluent through the monitoring apparatus.

A system for immediate analysis of contaminants in situ is needed to overcome the disadvantages of the previously available systems. There is also a need for a system that incorporates reliability and sensitivity in performing the necessary analyses that is low-cost and easy to maintain. It is, therefore, to the provision of such an instrument that the instant invention is directed.

SUMMARY

The present invention includes a self-propelled apparatus for analysis of a component contained in a fluid medium. The apparatus includes an analytical system and a conveyance system to move the analytical system through the fluid medium and facilitate fluid flow through the fluid conduit of the analytical system.

The analytical system includes a fluid inlet that receives fluid from the fluid medium and a fluid outlet, which is connected to the fluid inlet via a fluid conduit. The fluid conduit defines a fluid pathway. The fluid outlet dispels at least a portion of the fluid medium received by the fluid inlet. The analytical system further includes an analysis chamber, which is connected to the fluid conduit and positioned intermediate to the fluid inlet and the fluid outlet in the fluid pathway. The analytical system further includes a reagent system located within the analysis chamber to isolate the component. The analytical system also includes a sensor system, which is positioned within the analysis chamber and in communication with the fluid pathway, to sense the component.

The conveyance system may be removably attached to the analytical system. The conveyance system may include a propulsion system.

The self-propelled apparatus may further include a power source located within the conveyance system for providing power to the analytical system.

The analytical system may further include a means for transferring data.

The self-propelled apparatus may further include a tether connecting the analytical system and the conveyance system. The tether may be a transmission cable for transmitting data from the analytical system to the conveyance system. The tether may also be a power cable for providing power to the analytical system from a power source located in the conveyance system.

The sensor system may determine the concentration of the component. The sensor system may be an optical system, an electromechanical system, an electrical system, a gravitational system, a mass loading system, an ion trap system, a molecular trap system, or a particle trap system. The sensor system may also include a light source and a detector.

The self-propelled apparatus may also further include a pre-extractor connected to the fluid inlet of the analytical system to receive fluid from the fluid medium and transport the fluid to the fluid inlet.

The self-propelled apparatus may further include a burst reservoir located adjacent to the analysis chamber and in fluid communication with the analysis chamber.

The present invention also includes a method of using the self-propelled apparatus to analyze a component contained in a fluid medium. The method includes providing a self-propelled apparatus as described above, introducing the analytical system into the fluid medium to permit the flow of the fluid medium through the analytical system, and recording data on the component contained in the fluid medium using the sensor system.

The method may further include transmitting data from the analytical system to a remote location. As used herein, the term "remote" means that the data is transmitted to an apparatus not in immediate contact with the analytical system.

The method may also include determining the concentration of the component of the fluid medium.

The method may further include capturing the component contained in the fluid medium in the reagent system.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention includes a submersible, self-propelled apparatus for analysis of a component contained in a liquid medium. The apparatus includes an analytical system and a conveyance system to move the analytical system through the liquid medium and facilitate liquid flow through the liquid conduit of the analytical system.

Figure 1:
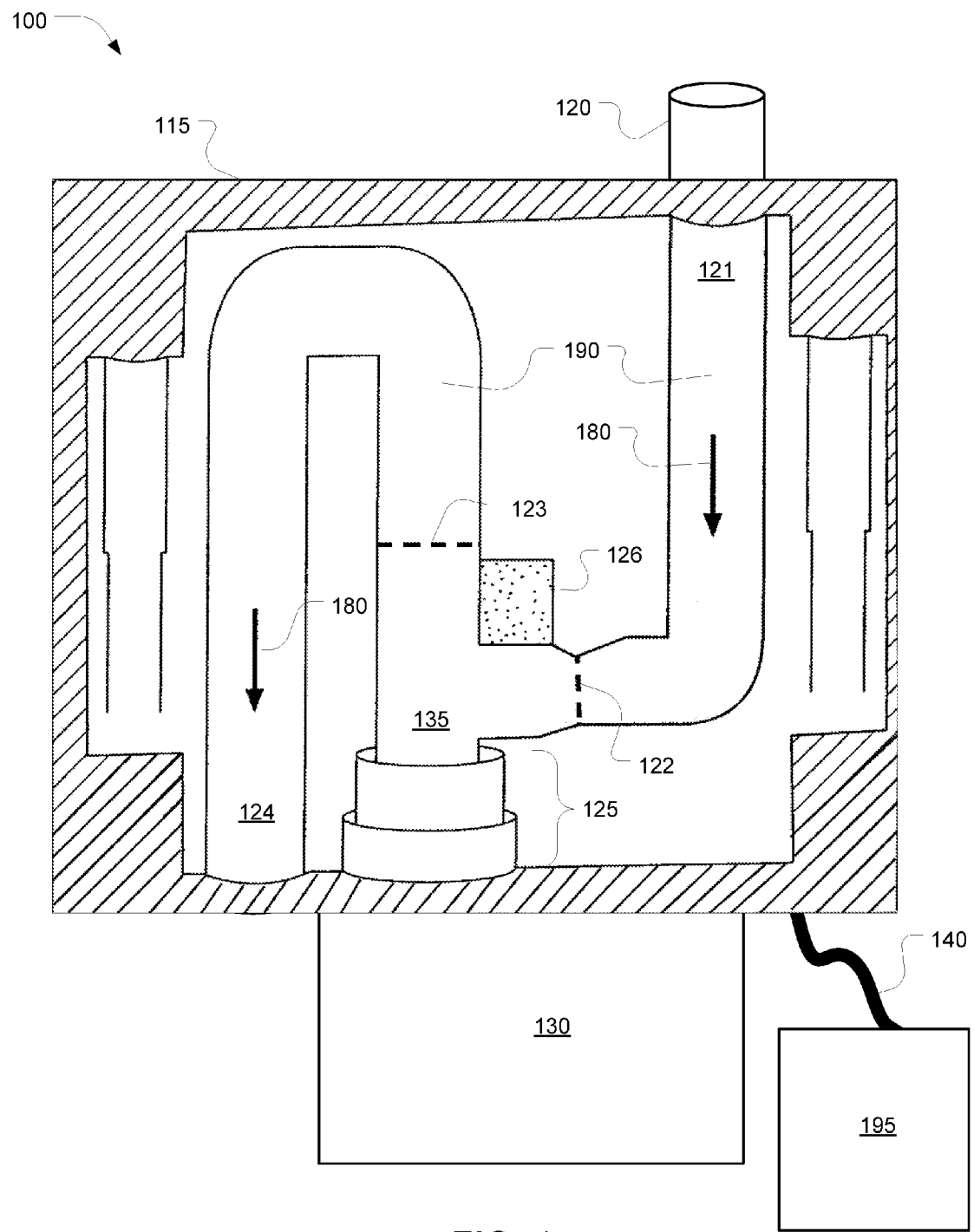
FIG. 1 is a diagram of a first configuration of the analytical system according to an embodiment of the present invention.
Figure 2:
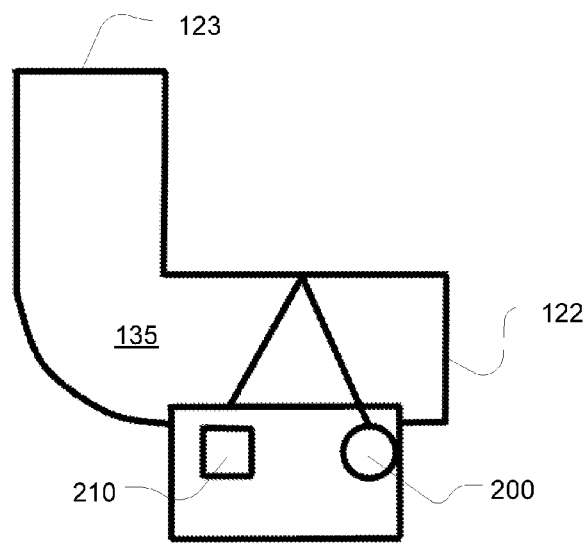
FIG. 2 is a diagram of the analysis chamber of the analytical system according to an embodiment of the present invention.
Figure 3:
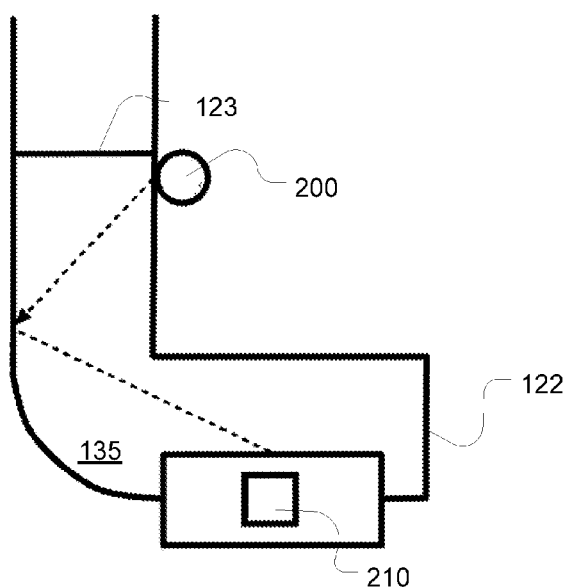
FIG. 3 is a diagram of a first configuration of the sensor system of the analytical system according to an embodiment of the present invention.
Figure 4:
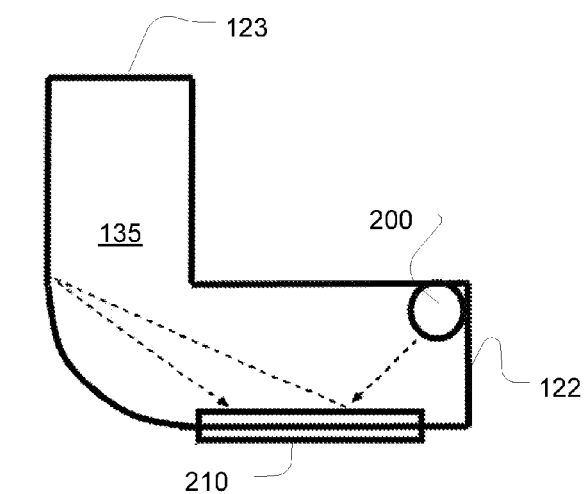
FIG. 4 is a diagram of a second configuration of the sensor system of the analytical system according to an embodiment of the present invention.

In an embodiment, as shown in FIG. 1, analytical system 100 includes detection portion 115 connected to support system 130. In an embodiment, detection portion 115 and support system 130 are encased in a housing (not shown) that may be any suitable housing as known to those of ordinary skill in the art for the environment of use. Detection portion 115 and support system 130 may be detachably connected, a single unit, or arranged to allow for reuse of desired components. Any desired geometry for the overall system may be chosen by one of ordinary skill in the art. FIG. 1 represents only one embodiment.

Detection portion 115 includes fluid inlet 121 for ingress of the fluid to be examined. Fluid inlet 121 may be co-extensive with the housing, protrude therefrom, or be recessed within the interior confines of the housing. Pre-extractor 120 may be also present at the proximal end of fluid inlet 121 if desired to separate deleterious material from entering detection portion 115. Detection portion 115 also includes fluid outlet 124, which dispels fluid from detection portion 115. Fluid inlet 121, as well as fluid outlet 124, may be formed of any suitable material as known to those of ordinary skill in the art. For example, a non-porous plastic that is inert to the environment can be used.

Fluid inlet 121 is connected to fluid outlet 124 via fluid conduit 190, which defines a fluid pathway. Fluid flows in the direction shown by arrows 180. Fluid is received at pre-extractor 120 (if present) and then moves through fluid inlet 121 and analysis chamber 135, and then exits through fluid outlet 124.

Located at the distal end of fluid inlet 121 is first separator 122 that blocks, at least temporarily, unwanted material from entering analysis chamber 135. First separator 122 may be any suitable separator, such as a filter, a screening material, or a semi-permeable membrane. First separator 122 is chosen for the milieu of use and for optimizing the effectiveness of performing a concentrating and screening function.

Second separator 123 is located in fluid communication with first separator 122 with the intermediate portion of the fluid conduit defining analysis chamber 135. Second separator 123, at least temporarily, prevents the component of interest from exiting analysis chamber 135. In addition, both first separator 122 and second separator 123 may have coatings applied to them to assist in the detection of the component, such as, but not limited to, reflective coatings that enhance optical characteristics of the analytical system 100. The fluid of interest exits analytical system 100 via fluid outlet 124.

Analysis chamber 135, by virtue of first separator 122 and second separator 123, also acts to concentrate the component of interest. Thus, the component of interest is substantially trapped within the confines of analysis chamber 135 so that sensor system 125 is able to respond to its presence. Sensor system 125 may be designed to respond to a threshold value of the component or may be chosen to actually quantify the concentration of the component contained in analysis chamber 135. In addition, sensor system 125 may be constructed to react to a plurality of components of interest.

Optionally, burst reservoir 126 may be included in detection portion 115. Burst reservoir 126 introduces a chemical enhancement into the analysis chamber 135 to aid the performance of sensor system 125. If a plurality of analyses are performed, burst reservoir 126 may be compartmentalized and serve to introduce a plurality of enhancements.

Support system 130 includes the electronic components necessary to support the function of the sensor system 125. This may include power supplies, either battery or cable supplied, as well as the support electronics necessary to run sensor system 125. In addition, any other necessary or desired support equipment may also be contained within this structure, including, but not limited to, telemetry devices, GPS units, and data storage units. Optionally, the power source and/or other support electronics are contained within conveyance system 195. Additionally, the self-propelled apparatus may also include a second power source. This second power source may be contained within conveyance system 195.

The self-propelled apparatus of the present invention further includes conveyance system 195. Analytical system 100 may be removably attached to conveyance system 195 by line 140. Line 140 may be a tethering line only or may also include a means for communication and a power source to analysis system 100 and means for feedback for the retrieval of data or other information from analysis system 100. For example, line 140 may be a transmission cable for transmitting data from analytical system 100 to conveyance system 195. As another example, line 140 may be a power cable for providing power to analytical system 100 from a power source located on conveyance system 195. Conveyance system 195 itself may be a tether. If conveyance system 195 is a tether, it may be connected to a second conveyance system (not shown). Any suitable means known to those of ordinary skill in the art may be used for any of the desired embodiments as described above. Conveyance system 195 may be a watercraft or aircraft of any description, either manned or remote controlled, suitable as a means for transporting analytical system 100 through the fluid to be analyzed.

Figure 6:
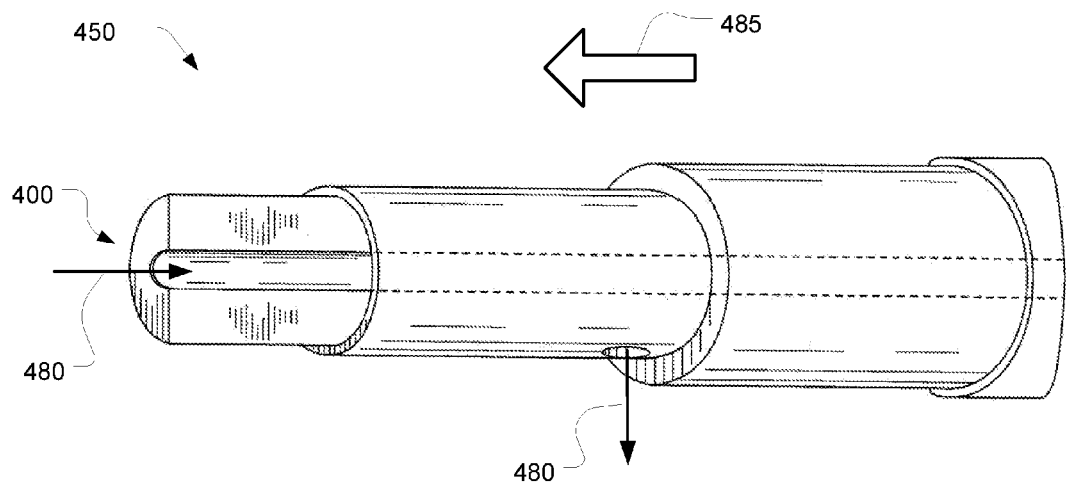
FIG. 6 is a diagram of the third configuration of the analytical system on board a projectile according to an embodiment of the present invention.

In an embodiment of the present invention, conveyance system 195 is a propulsion system. The propulsion system may be any either an integral system to the overall device or a detachable propulsion system that may even be replaceable if the overall system is intended to be reusable. The propulsion system may be a renewable system. Examples of propulsion system include, but are not limited to: bullets, artillery shells, torpedoes, drop projectiles, fired projectiles, missiles, and other munition systems. The propulsion system may also be detachable from the remainder of the apparatus. In addition, telemetry systems may be included for relaying the desired data back to a monitoring station. In one embodiment, analytical system 100 is connected to propulsion system. In another embodiment, analytical system 100 is on-board propulsion system 450, as shown in FIG. 6. In this embodiment, as propulsion system 450 moves through a fluid medium in the direction shown by arrow 485, fluid flows into and through analysis system 400 in the direction shown by arrows 480.

Conveyance system 195 (and the propulsion system) serves not only to transmit analytical device 100 to the location of interest, but also to provide the fluid flow within analytical system 100 to effect the analytical functions. The sampling function may occur while the propulsion system is actively powering the device, or after the propulsion system is spent in a free-drift mode.

Additional power sources may also be present for telemetry, GPS, electronic controls and other communication purposes. Further instrumentation may also include receivers, steering devices, and other ground or ship communication devices, so that adjustments may be made to the flight path of the apparatus after it is deployed. In addition, a second propulsion system may be incorporated into the apparatus so that it may be transmitted after a period of time to a further location, such as a pick-up location. An aerial-type device, such as a kite, balloon, or aircraft, may be used for overland applications. Flotation devices such as a watercraft may be used for aquatic applications.

Conveyance system 195 may be detachable so that analytical system 100 may be released and gravity acts to propel it through the fluid medium. In this embodiment, telemetry may also be used to transmit the data or other results back to a monitoring station or the analytical system 100 may be retrieved. Also contemplated is the use of balloons or kites, with sampling taking place during ascent and travel. If detachable cords are used, sampling may also occur during gravitational descent.

Because gravity or the motion of conveyance system 195 are used to impel the flow of fluid through analytical system 100, the need for the auxiliary pumps of the prior art is obviated. This enables the instant device to be reduced in size and simplifies the power requirements of the analytical system 100. In addition, analysis chamber 135 may be a microsized portion of the overall system, so that minute or trace amounts of a component of interest may be captured and detected.

Figure 5:
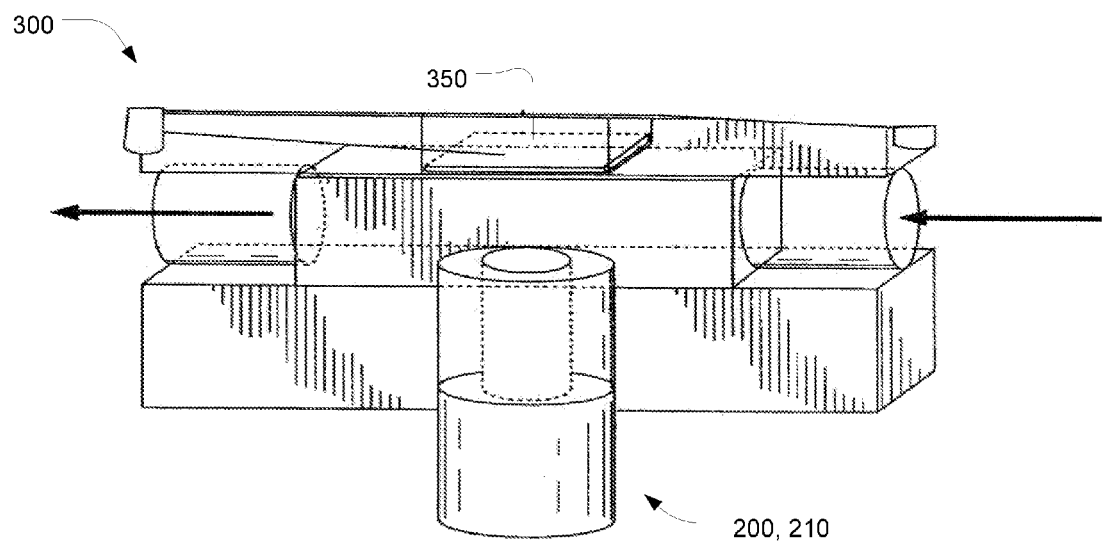
FIG. 5 is a diagram of a second configuration of the analytical system according to an embodiment of the present invention.

Analysis chamber 135 may be constructed in any geometry necessary to enhance the performance of sensor system 125, the component of interest, and the fluid medium. Three example geometries for an optical sensor detection system are shown in FIGS. 2 through 5. In each of these examples, light source 200 emits a light beam through analysis chamber 135 to detector 210. Other geometries are also available and are considered as design variations to one of ordinary skill in the art, including a linear arrangement as shown in FIG. 5.

In addition to a single detection system, it is contemplated that a flow splitting arrangement may also be incorporated so that multiple discreet detections of the same or different component may be made simultaneously. In addition, either one or both of separators 122 and 123 may be omitted depending on the sensor system used. Reagent systems that trap the component of interest or assist in the detection of the component may also be used. A diagram of an embodiment using reagent trap 350 is shown in FIG. 5 in conjunction with a linear, non-membrane detection system 300. Here, reagent trap 350 is used for isolation of the desired component.

In addition to optical sensors, various other types of sensors may be employed. Example sensors include, but are not limited to, electrical, electrochemical, gravimetric, mass loading and ion or molecular and particle traps. Various configurations of analysis chamber 135 to accommodate these types are systems are considered within the scope of knowledge of one of ordinary skill in the art. In addition, a threshold-type of sensor may also be incorporated into analytical system 100, with comparison to a pre-determined level being the output of choice.

Modification and variation can be made to the disclosed embodiments of the instant invention without departing from the scope of the invention as described. Those skilled in the art will appreciate that the applications of the present invention herein are varied, and that the invention is described in one preferred embodiment. Accordingly, additions and modifications can be made without departing from the principles of the invention. Particularly with respect to the claims it should be understood that changes may be made without departing from the essence of this invention. In this regard it is intended that such changes would still fall within the scope of the present invention. Therefore, this invention is not limited to the particular embodiments disclosed, but is intended to cover modifications within the spirit and scope of the present invention as defined in the appended claims.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A submersible, self-propelled apparatus for analysis of a component contained in a liquid medium, the apparatus comprising:
    an analytical system comprising
        a liquid inlet to receive liquid from the liquid medium,
        a liquid outlet connected to the liquid inlet via a liquid conduit that defines a liquid pathway, wherein the liquid outlet dispels at least a portion of the liquid medium received by the liquid inlet,
        an analysis chamber connected to the liquid conduit, positioned intermediate to the liquid inlet and the liquid outlet in the liquid pathway,
        a reagent system located within the analysis chamber to isolate the component, and
        a sensor system positioned within the analysis chamber and in communication with the liquid pathway to sense the component; and
    a conveyance system to move the apparatus through the liquid medium and facilitate liquid flow through the liquid conduit when the apparatus is submersed in the liquid medium.

2. The self-propelled apparatus of claim 1, wherein the conveyance system comprises a propulsion system.

3. The self-propelled apparatus of claim 1, further comprising:
    a power source located within the conveyance system for providing power to the analytical system.

4. The self-propelled apparatus of claim 1, wherein the conveyance system is removably attached to the analytical system.

5. The self-propelled apparatus of claim 1, wherein the apparatus further comprises a means for transferring data.

6. The self-propelled apparatus of claim 1, wherein the sensor system determines the concentration of the component.

7. The self-propelled apparatus of claim 1, wherein the sensor system of the analytical system is selected from the group consisting of an optical system, an electrochemical system, an electrical system, a gravimetric system, a mass loading system, an ion trap system, a molecular trap system, and a particle trap system.

8. The self-propelled apparatus of claim 1, wherein the analytical apparatus further comprises a burst reservoir positioned adjacent to the analysis chamber and in liquid communication with the analysis chamber.

9. The self-propelled apparatus of claim 1, further comprising:
    a pre-extractor connected to the liquid inlet of the analytical system to receive liquid from the liquid medium and transport the liquid to the liquid inlet.

10. The self-propelled apparatus of claim 1, further comprising:
    a tether connected to the analytical system and the conveyance system.

11. A method of analyzing a component contained in a liquid medium using a submersible, self-propelled apparatus, the method comprising of the steps:
    providing a submersible, self-propelled apparatus comprising:
        an analytical system comprising
            a liquid inlet to receive liquid from the liquid medium,
            a liquid outlet connected to the liquid inlet via a liquid conduit that defines a liquid pathway, wherein the liquid outlet dispels at least a portion of the liquid medium received by the liquid inlet,
            an analysis chamber connected to the liquid conduit, positioned intermediate to the liquid inlet and the liquid outlet in the liquid pathway,
            a reagent system located within the analysis chamber to isolate the component, and
            a sensor system positioned within the analysis chamber and in communication with the liquid pathway to sense the component; and
        a conveyance system to move the apparatus through the liquid medium and facilitate liquid flow through the liquid conduit when the apparatus is submersed in the liquid medium
    introducing the analytical system into the liquid medium to permit the flow of the liquid medium through the analytical system; and
    recording data on the component contained in the liquid medium using the sensor system.

12. The method of claim 11, wherein the conveyance system comprises a propulsion system.

13. The method of claim 11, wherein the conveyance system is removably attached to the analytical system.

14. The method of claim 11, wherein the self-propelled apparatus further comprises a power source located within the conveyance system for providing power to the analytical system.

15. The method of claim 11, wherein the self-propelled apparatus further comprises a tether connected to the analytical system and the conveyance system.

16. The method of claim 11, wherein the self-propelled apparatus further comprises a means for transmitting data.

17. The method of claim 16, further comprising:
    transmitting data from the analytical system to a remote location.

18. The method of claim 11, further comprising:
    determining the concentration of the component of the liquid medium.

19. The method of claim 11, wherein the sensor system of the analytical system is selected from the group consisting of an optical system, an electrochemical system, an electrical system, a gravimetric system, a mass loading system, an ion trap system, a molecular trap system, and a particle trap system.

20. The method of claim 11, wherein the analytical system further comprises a burst reservoir positioned adjacent to the analysis chamber and in liquid communication with the analysis chamber.

21. The method of claim 11, wherein the self-propelled apparatus further comprises a preextractor connected to the liquid inlet of the analytical system to receive liquid from the liquid medium and transport the liquid to the liquid inlet.

22. The method of claim 11, further comprising:
  capturing the component contained in the liquid medium in the reagent system.

* * * * *